United States Patent [19]

Campbell et al.

[11] 4,413,126

[45] Nov. 1, 1983

[54] PREPARATION OF ISOQUINOLINE DERIVATIVES USEFUL AS IMMUNE REGULANTS

[75] Inventors: Jack B. Campbell; Edward R. Lavagnino, both of Indianapolis, Ind.

[73] Assignee: Eli Lilly and Company, Indianapolis, Ind.

[21] Appl. No.: 386,833

[22] Filed: Jun. 9, 1982

[51] Int. Cl.³ .................... C07D 471/06; A61K 31/47
[52] U.S. Cl. ........................................ 546/52; 424/258
[58] Field of Search .................................... 546/52, 66

[56] References Cited

U.S. PATENT DOCUMENTS 4,040,968  8/1977  Harris ............................ 252/51.5 A
4,097,450  6/1978  Papenfuhs et al. ............... 260/42.21

OTHER PUBLICATIONS

CA 51:2745h, 2746b, 2746g, and 2747c (1957), abstracting *J. Soc. Org. Synthet. Chem.*, Japan, 13, 80, 175, 228, and 413 (1955), respectively.
*Collection Czech. Chem. Commun.*, 28, 1292 (1963), as reported in CA 59:4070f (1963).
CA 53:18499a (1959) which abstracts French Pat. No. 1,111,620.
*J. Indian Chem. Soc.*, 55 (11), 1159 (1976), as reported in CA 87:102228u (1977).
*J. Het. Chem.*, 10 (5), 705 (1973).
CA 68:2848k (1968).
CA 64:14323f (1966).
CA 53:1722b (1959).
CA 69:20388k (1968).
CA 69:39754y (1968).
CA 88:37691u (1978).
CA 73:4944r (1970).
CA 64:19834f (1966).
CA 60:6955d (1964).
CA 71:92624y (1969).
CA 66:89913h (1967).
CA 64:16029c (1966).
CA 84:32593w (1976).
CA 81:14718z (1974).
CA 55:1012i (1961).
CA 80:84160q (1974).

*Primary Examiner*—Mark L. Berch
*Attorney, Agent, or Firm*—Leroy Whitaker; Arthur R. Whale

[57] ABSTRACT

This invention provides for a process of preparing certain trifluoromethyl substituted 7H-benzimidazo[2,1-a]benz[de]isoquinoline-7-ones.

4 Claims, No Drawings

PREPARATION OF ISOQUINOLINE DERIVATIVES USEFUL AS IMMUNE REGULANTS

BACKGROUND OF THE INVENTION

Recently, immune suppressant agents have come into prominence because of their use during transplants of organs from one human to another, and in particular in connection with organ transplant operations such as heart and kidney transplants. It is part of the defense mechanism of humans to remove foreign antigens (in this case, produced by the transplanted organ) by the immune reaction. Thus, in all of the organ transplant operations, it has been necessary to give large doses of an immune suppressant prior to the operation and continuing thereafter in order to prevent the host from rejecting the donor organ.

The immune response is composed of a sequence of cellular transformations and biochemical events leading to a bimodal response to foreign substances (antigens). Cells which are to participate in the response evolve from stem cells which originate in the bone marrow and are seeded out to the peripheral lymphoid organs. From these latter sites, following antigenic stimulus, the body's response is mounted in the form of plasma cells (which produce antibody) and specific immune lymphocytes. Antibody is released into the circulatory system and thus may act at a distance from the producing cell (humoral immunity). Specific immune lymphocytes also enter the circulatory system and act at the site of injury (cellular immunity). The reaction of antibody with antigen triggers the release of histamine from basophilic leucocytes; histamine, in turn, alters the permeability of blood vessels, speeding the influx of body antibody and specific immune lymphocytes into the sites of injury. Thus, the immune response is composed of a series of biochemical events in a sequence of cells at various sites in the body. It can be altered—suppressed, in the case of the compounds herein discussed—at a number of biochemical or cellular developmental sites.

Antihistamines only affect a secondary reaction in the immune response, having no direct effect on antibody-producing cells or on specific immune lymphocytes. A number of agents, currently in use as immuno-suppressive drugs, act further back in the chain of events called herein the immune response. Certain anti-inflammatory steroids, e.g., cortisone, suppress production of antibody and specific immune lymphocytes, but also radically deplete normal lymphoid tissue and have other undesirable side effects. Certain anti-neoplastic drugs e.g., azathioprine, cyclophosphamide, and methotrexate, are employed as immunosuppressives, but they alo deplete normal lymphoid tissue and radically depress other bone-marrow-derived cells. The general cytotoxicity of the latter drugs is to be expected in view of their having been selected on the basis of toxicity against a spectrum of cell types.

It is an object of this invention to provide compounds which alter the immune response in mammals by acting on cells functioning in the immune response, but which avoid certain side-effects and other undesirable attributes of compounds currently available as immune regulants.

Certain substituted 7H-benzimidazo[2,1-a]benz[de]isoquinoline-7-ones, are named and numbered according to the Ring Index, The American Chemical Society, number 5818, as follows:

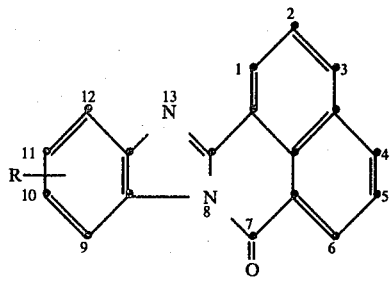

and their method of preparation are taught in the literature. Okazaki, et al., *J. Soc. Org. Synthet. Chem., Japan*, 13, 80, 175, 228, and 413 (1955), describe the preparation of 10- and 11-substituted compounds as represented by Formula I wherein R is hydrogen, methyl, methoxy, and chloro. Similarly, Arient and Marhan, *Collection Czech. Chem. Commun.*, 28, 1292 (1963), describe the synthesis of related compounds wherein R is chloro, methyl, nitro, and amino. Each citation uses the same two methods of preparation. The first method employs the reaction between 1,8-naphthalic acid anhydride and appropriately substituted o-phenylenediamines, the latter either being prepared and isolated or formed in situ from the appropriate o-nitroaniline precursor. The in situ preparation may be done prior to the introduction of the anhydride or in the presence of the anhydride.

The second method produces an intermediate N-substituted-naphthalimide from the reaction of naphthalic anhydride with the appropriately substituted o-nitroaniline, which in a second step can be converted to the final product (i.e., compounds as represented in Formula I) by chemical reduction and condensation.

Both methods were more recently employed in a patent (U.S. Pat. No. 4,097,450) describing the reaction of o-phenylenediamines and o-nitroanilines with 3,6-dihydroxynaphthalic acid anhydride to prepare 2,5-dihydroxy congeners of the compounds represented by Formula I.

In all three citations above it has been recognized that the (second) method utilizing o-nitroanilines is superior to the first method when the corresponding o-phenylenediamine reaction can and does give two isomers. For example, Okazaki (supra, p. 413) demonstrated a 42:58 ratio of 10- to 11-chloro isomers when 3,4-diaminochlorobenzene was reacted with naphthalic anhydride, whereas pure isomers could be obtained when the appropriately substituted o-nitroanilines were first reacted with the anhydride and followed with chemical reduction and condensation.

It has also been taught (Arient and Marhan, supra) how various derivatives, such as where R is chloro, can be prepared from compounds of Formula I where R is nitro, upon reduction to the aniline (R is $NH_2$) and subsequent transformations via the Sandmeyer reaction.

In the above references the compounds of Formula I were found to possess qualities suitable for their use as dyes and pigments. More recently several derivatives are also said to be useful as epoxy hardeners and as thickening agents for greases.

SUMMARY OF THE INVENTION

This invention provides for the use of substituted 7H-benzimidazo[2,1-a]benz[de]isoquinoline-7-ones represented by the formula II

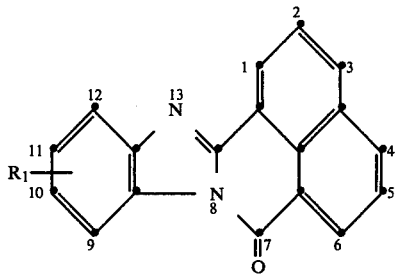

and pharmaceutically acceptable salts thereof, as agents capable of altering the immune response in mammals and formulations containing the same. In the foregoing formula, $R_1$ represents bromo, chloro, fluoro, or trifluoromethyl, and is at the 10 or 11 position. This invention also provides for the novel trifluoromethyl and bromo compounds of Formula II and a new method for the preparation of the novel trifluoromethyl compounds described above.

DETAILED DESCRIPTION AND PREFERRED EMBODIMENT

The preferred compounds of this invention are those of Formula II wherein $R_1$ is at the 11 position. Especially preferred is 11-trifluoromethyl-7H-benzimidazo[2,1-a]benz[de]isoquinoline-7-one and pharmaceutically acceptable salts thereof.

The compounds of this invention as represented by Formula II can be prepared by the condensation of substituted o-phenylenediamines with naphthalic anhydride. The o-phenylenediamines may be prepared from the appropriate o-nitroaniline precursors either by catalytic hydrogenation or chemical reduction. The diamine thus produced may be isolated and subsequently reacted with the anhydride, prepared in situ for later condensation with the anhydride, or prepared in situ in the presence of the anhydride. The condensation is completed by heating at elevated temperatures, typically in the range of about 50°–180° C. Suitable hydrogenation catalysts include Raney nickel, palladium-on-carbon, platinum oxide, sulfided platinum-on-carbon, and the like. Solvents which are inert to hydrogenation conditions such as ethanol, acetic acid, or tetrahydrofuran may be suitably employed as the reaction medium. Chemical means of reduction include zinc or iron dust or stannous chloride in the presence of an acid, such as hydrochloric acid. Generally in the practice of this invention, molar equivalents of the o-phenylenediamine or o-nitroaniline reactant and anhydride are employed. However, an excess of either reactant can be used if desired without an adverse effect on the yield. By this process, two isomers of compounds as represented by Formula II are formed from a singly substituted o-phenylenediamine or o-nitroaniline. The products can be recovered by evaporation of the solvent and purification can be accomplished by conventional methods such as crystallization and/or chromatography.

In most cases, the anhydride can alternatively be condensed by heating with the appropriate o-nitroaniline in a suitable inert solvent such as acetic acid to produce the intermediate N-(substituted-o-nitrophenyl)naphthalimide. Subsequent reduction and heating as described above then converts the substituted naphthalimide to a single isomer of Formula II.

Although the latter method is preferred in preparing isomerically pure compounds, it has been found to be inoperable in certain cases. For instance, while the reaction of 3,4-diaminobenzotrifluoride with naphthalic anhydride gives the expected 10- and 11-trifluoromethyl isomers of Formula II which must then be separated by chromatography, exposure of the anhydride to 4-amino-3-nitrobenzotrifluoride in the manner described above unexpectedly gives no desired imide intermediate. However, this invention further provides an alternative method of producing isomerically pure compounds represented by Formula II wherein $R_1$ is trifluoromethyl in a direct and efficient manner.

We have found that when the alkali metal salt of naphthalimide, prepared, for example, by the action of an alkali metal base such as a carbonate or hydroxide upon naphthalimide, is heated in a high boiling inert solvent with a 4- or 5-trifluoromethyl substituted o-nitrohalobenzene, preferably in the presence of an alkali metal halide catalyst such as potassium iodide or potassium fluoride, the appropriate N-(trifluoromethyl-substituted-o-nitrophenyl)-naphthalimide can be prepared. This intermediate N-substituted naphthalimide can then be reduced and condensed in the manner previously described above.

Temperatures which are effective in accomplishing the reaction between naphthalimide and the trifluoromethyl-substituted-o-nitrohalobenzene include the range of 50°–200° C., with 100°–180° C. being preferred and 140°–160° C. being most preferred. Suitable solvents are those which are inert to the reaction process and can accomplish the temperature desired, such as diglyme, N,N-dimethylformamide, dioxane, and the like. The solvents should be essentially free from water to minimize any undesirable interaction with the o-nitrohalobenzene reagents. Bases which are capable of forming the naphthalimide salt are employed; preferred are alkali metal carbonates and hydroxides such as potassium carbonate and sodium hydroxide. Although not critical to this invention, we have found that small amounts of alkali metal halides, such as potassium fluoride or potassium iodide, serve to catalyze the reaction and it is therefore desirable to have such compounds present in the reaction mixture to facilitate the reaction process.

Generally in the practice of this invention, the naphthalimide is allowed to react in the presence of 1.0–1.5 molar equivalents of base and 1–2 molar equivalents of the o-nitrohalobenzene, although these ratios are not meant to be limiting as to the scope of this invention.

The pharmaceutically acceptable acid addition salts of this invention include salts derived from inorganic acids such as hydrochloric acid, nitric acid, phosphoric acid, sulfuric acid, hydrobromic acid, hydroiodic acid, and the like, as well as salts derived from nontoxic strong organic acids such as aliphatic and aromatic sulfonic acids. Such pharmaceutically acceptable salts thus include sulfate, nitrate, chloride, bromide, iodide, benzenesulfonate, toluenesulfonate, chlorobenzenesulfonate, xylenesulfonate, methanesulfonate, propanesulfonate, naphthalene-1-sulfonate, naphthalene-2-sulfonate, methyl p-toluenesulfonate, and the like salts.

Naphthalic anhydride and naphthalimide are commercially available. The o-nitrohalobenzene, o-nitroaniline, and o-phenylenediamine compounds which are required as reactants are either commercially available or can be prepared by the known methods of amination, halogenation, nitration or reduction of suitable aromatic precursors. The required benzotrifluoride reactants can be prepared by the fluorination of the corresponding benzoic acids with sulfur tetrafluoride.

The present invention is also directed to a method for suppressing the immune reaction in mammals. Such suppression includes the suppression of immune response engendered whenever the mammalian body forms antibodies and reactive cells in response to the presence of foreign protein. The practical application of immunosuppressive activity is varied. A prominent application of immunosuppressive activity is in the transplanting of organs, but immunosuppressive activity can also be advantageously employed in the therapy of the various diseases known collectively as "autoimmune" diseases. Representative auto-immune diseases include auto-immune hemolytic anemia, idiopathic thrombocytopenic purpura, lupus erythematosus, lupoid hepatitis, lupus nephritis, glomerulonephritis, the nephrotic syndrome, Goodpasture's syndrome, Wegener's granulomatosis, schleroderma, Sezary's disease, psoriasis, uveitis, rheumatoid arthritis, ulcerative colitis, thyroiditis and mumps orchitis.

In implementing the present immunosuppressing method, administration can be by the oral or parenteral routes. The precise amount of active agent to be employed varies from compound to compound. However, the compounds have a high therapeutic index, so that effective, non-toxic doses, in each case, extend over a wide range. Depending upon the test system, this range, for the more active members of the series tested in small mammals, extends from 0.2 to 25 mg./kg. per day. Other compounds of the series require more, such as up to 100 mg./kg. per day or more, in small mammals. Given the relationship between small and large animal doses seen with other drugs—e.g., the human dose of the immunosuppressant, azathioprine is generally 1–2 mg./kg., whereas the mouse dose is approximately 50 mg./kg. (see also *Cancer Chemotherapy Reports*, 50, 219 (1966))—the anticipated effective human dose levels would be correspondingly lower than in small mammals, such as from 0.05–10 mg./kg. per day.

In carrying out the therapeutic method of the present invention, it is generally preferred to employ a composition comprising the active agent and one or more adjuvants suited to the particular route of administration. Compositions for oral administration may be either solid: e.g., capsules, tablets, pills, powders, etc., or liquid: e.g., emulsions, solutions, suspensions, syrups, elixirs, etc., combined with conventional adjuvants. In the case of solid formulations, suitable adjuvants include inert substances such as sucrose, lactose, and starch. In the case of liquid formulations, suitable adjuvants include water, mineral oil, etc. When an aqueous solution is desired, an acid addition salt is conveniently employed. Either solid or liquid formulations can include lubricating agents, wetting agents, emulsifying and suspending agents, preserving agents, sweetening agents or flavoring agents.

In the instance of parenteral administration, the compounds of the present invention are formulated in a suitable sterile, injectable liquid. For example, a pharmaceutically acceptable acid-addition salt formed with a non-toxic acid is used in an isotonic salt solution for I.V. or other injection route.

A preferred formulation is one in dosage unit form adapted for oral administration to obtain an immunosuppressive effect, which comprises, per dosage unit, an immunosuppressive, non-toxic amount within the range from about 0.2 to about 1000 milligrams of the present active agent, preferably in the range of 2 to 250 milligrams, and a pharmaceutical diluent.

The following examples illustrate the present invention.

EXAMPLE 1

Preparation of 11-(trifluoromethyl)-7H-benzimidazo[2,1-a]benz-[de]isoquinoline-7-one

A.

2-[2-nitro-4-(trifluoromethyl)phenyl]-1H-benz-[de]isoquinoline-1,3(2H)-dione

Eight-tenths mole (157.6 g.) of 1,8-naphthalimide, 260 g. (1.15 m.) of 4-chloro-3-nitrobenzotrifluoride, 64 g. (0.46 m.) of anhydrous potassium carbonate, about 4 g. (0.024 m.) of potassium iodide, and 2400 ml. of dry N,N-dimethylformamide were allowed to reflux under a nitrogen atmosphere for about 8 hours. The reaction mixture was allowed to cool to room temperature and the reaction vessel was then chilled in an ice-bath. The resulting precipitate was filtered, washed with water, and dried in vacuo to yield crude 2-[2-nitro-4-(trifluoromethyl)phenyl]-1H-benz[de]isoquinoline-1,3-(2H)-dione.

B.

11-(Trifluoromethyl)-7H-benzimidazo[2,1-a]benz-[de]isoquinoline-7-one

2-[2-nitro-4-(trifluoromethyl)phenyl]-1H-benz-[de]isoquinoline-1,3(2H)-dione, 134.3 g. (0.347 m.), was hydrogenated at 55° C. in 600 ml. of glacial acetic acid with 15 g. of palladium-on-carbon (5 percent) at 60 psi. The temperature rose to about 100° C., and after 1.5 hours, three equivalents of hydrogen were absorbed with the temperature returning to room temperature. The reaction mixture was heated to boiling and filtered to remove the catalyst. Upon cooling, the precipitated product was collected and washed with 2B ethanol. Recrystallization from N,N-dimethylformamide yielded about 69.2 g. (59 percent yield) of 11-(trifluoromethyl)-7H-benzimidazo[2,1-a]benz[de]isoquinoline-7-one, m.p. about 212°–214° C.

Analysis: $C_{19}H_9F_3N_2O$; Calc: C, 67.46; H, 2.68; N, 8.28; F, 16.85; Found: C, 67.19; H, 2.48; N, 7.99; F, 16.83.

EXAMPLE 2

Alternate preparation of 10- and 11-(trifluoromethyl)-7H-benzimidazo[2,1-a]benz-[de]isoquinoline-7-one One-tenth mole (20.6 g.) of 4-amino-3-nitrobenzotrifluoride was catalytically reduced to the respective diamine in 350 ml. of 2B ethanol using about 3 g. of Raney nickel at about 60 psi. After the uptake ceased, the catalyst was filtered off and the filtrate was heated with 19.8 g. (0.1 m.) of naphthalic acid anhydride in a sealed bomb at 180° C. for about 16 hours. Upon cooling, the resulting solid was collected by filtration and recrystallized from ethyl acetate. Additional material was recovered by adding water to the above filtrate, extracting with ethyl acetate, and evaporating the ethyl acetate. Crystallization from ethanol resulted in material with a m.p. about 198° C. (dec.). Total weight recovered from both crystallizations was 16.9 g. (50 percent yield). Thin layer chromatography on silica gel (eluting solvent:toluene/ethyl acetate, 4:1) revealed the presence of two major components in approximately equal amounts.

When 10.0 g. of the above mixture were subjected to reverse-phase high pressure liquid chromatography, 1.3 g. of the less polar product, 11-(trifluoromethyl)-7H-benzimidazo[2,1-a]benz[de]isoquinoline-7-one, yellow crystals from ethyl acetate, m.p. about 217°-219° C., and 1.8 g. of the more polar product, 10-(trifluoromethyl)-7H-benzimidazo[2,1-a]benz[de]isoquinoline-7-one, yellow crystals from ethyl acetate, m.p. about 237°-239° C., were recovered.

EXAMPLE 3

Preparation of 13-methyl-7-oxo-11-(trifluoromethyl)-7H-benzimidazo[2,1-a]benz[de]isoquinolinium 4-methylbenzenesulfonate Six grams (0.018 m.) of 11-(trifluoromethyl)-7H-benzimidazo[2,1-a]benz[de]isoquinoline-7-one were heated to about 100° C. in 25 ml. of methyl p-toluenesulfonate for about 16 hours under a nitrogen atmosphere. After cooling, the solution was poured into ether. The solids were collected and recrystallized twice from methanol/ether to give 4.7 g. (50.5 percent yield) of the desired product, m.p. about 263°-265° C.

Analysis: $C_{27}H_{19}F_3N_2O_4S$; Calc.: C, 61.83; H, 3.65; N, 5.34; Found: C, 61.54; H, 3.64; N, 5.11.

EXAMPLE 4

Preparation of 10- and 11-chloro-7H-benzimidazo[2,1-a]benz[de]isoquinoline-7-one Following the procedure of Example 2, 14.2 g. (0.1 m.) of 4-chloro-2-nitroaniline were catalytically reduced with 5% sulfided platinum-on-carbon and reacted with 19.8 g. (0.1 m.) of naphthalic anhydride to give the mixture of the 10- and 11-chloro isomers, in a 61% yield, m.p. about 200°-203° C. (recrystallized from N,N-dimethylformamide). Preparative HPLC and recrystallization from ethyl acetate gave the pure isomers.

11-chloro-7H-benzimidazo[2,1-a]benz[de]isoquinoline-7-one m.p. about 233°-235° C.

Analysis: $C_{18}H_9ClN_2O$; Calc.: C, 70.95; H, 2.98; N, 9.19; Found: C, 70.68; H, 3.16; N, 9.16.

10-chloro-7H-benzimidazo[2,1-a]benz[de]isoquinoline-7-one m.p. about 228°-230° C.

Analysis: $C_{18}H_9ClN_2O$; Calc.: C, 70.95; H, 2.98; N, 9.19; Found: C, 70.68; H, 2.87; N, 9.34.

EXAMPLE 5

Preparation of 10- and 11-bromo-7H-benzimidazo[2,1-a]benz[de]isoquinoline-7-one

Following the procedure of Example 2, 21.7 g. (0.1 m.) of 4-bromo-2-nitroaniline were catalytically reduced in 100 ml. of acetic acid with 5% sulfided platinum-on-carbon. After filtration of the catalyst, 19.8 g. (0.1 m.) of naphthalic anhydride were added in 300 ml. of 2B ethanol. After heating and cooling as described in Example 2, the products were recovered by filtration in a 40% yield, m.p. about 186°-188° C. (recrystallized from N,N-dimethylformamide). Preparative HPLC and recrystallization from ethyl acetate gave the pure isomers.

11-bromo-7H-benzimidazo[2,1-a]benz[de]isoquinoline-7-one m.p. about 220°-222° C.

Analysis: $C_{18}H_9BrN_2O$; Calc.: C, 61.91; H, 2.60; N, 8.02; Found: C, 61.85; H, 2.73; N, 7.86.

10-bromo-7H-benzimidazo[2,1-a]benz[de]isoquinoline-7-one m.p. about 208°-210° C.

Analysis: $C_{18}H_9BrN_2O$; Calc.: C, 61.91; H, 2.60; N, 8.02; Found: C, 61.95; H, 2.54; N, 7.76.

EXAMPLE 6

Preparation of 10- and 11-fluoro-7H-benzimidazo[2,1-a]benz[de]isoquinoline-7-one Following the procedure of Example 2, 15.6 g. (0.1 m.) of 4-fluoro-2-nitroaniline were catalytically reduced in 400 ml. of 2B ethanol with Raney nickel. After filtration of the catalyst, 19.8 g. (0.1 m.) of naphthalic anhydride were added, and after heating and cooling as described in Example 2, the products were recovered by filtration. Crystallization from tetrahydrofuran resulted in a 45 percent yield of the isomer mixture, m.p. about 215°-217° C. Preparative HPLC of about 5 g. of the mixture followed by crystallization from tetrahydrofuran gave 1.6 g. of 11-fluoro-7H-benzimidazo[2,1-a]benz[de]isoquinoline-7-one, m.p. about 228°-230° C., and a small amount of the 10-fluoro isomer. 11-fluoro-7H-benzimidazo[2,1-a]benz[de]isoquinoline-7-one Analysis: $C_{18}H_9FN_2O$; Calc.: C, 75.00; H, 3.15; N, 9.72; Found: C, 75.24; H, 3.21; N, 9.75.

EXAMPLES 7-19

Mouse Hemagglutinin assay, oral administration (pooled serum assay procedure)

Groups of five 20-gram, male, random-bred, Swiss mice received intravenous injections of $5 \times 10^7$ sheep red blood cells. The cells for these injections were prepared from lamb's blood (collected in Alsever's solution) by washing three times with 0.85 percent saline. Nine daily doses of each compound to be tested, solubilized in polyethylene glycol 400, were administered orally in 0.1 ml. doses, commencing three days prior to red blood cell injection. Several dose levels of each compound were employed, at 2-fold increments. A control group of mice, receiving a red blood cell injection and nine daily doses of vehicle instead of drug, was included. Six days after the antigen injections, the mice were bled by cardiac puncture and the blood from each 5-mouse group pooled. The sera from the pools, following complement inactivation (56° C. for 30 minutes), were assayed from hemagglutinin content using an "Autotiter 10" apparatus (Ames Div., Miles Laboratories) programmed to prepare serial 2-fold saline dilutions of the test sera in 0.25 percent sheep red blood cell suspension in microtitration trays. Following incubation of the trays for 3 hours at 37° C., the hemagglutination patterns were graded. A 4-fold (75 percent) or greater antibody reduction (in the test serum as compared with the control serum) was considered significant. The results were expressed as the minimum effective dose ("MED")—the lowest drug dose producing 75 percent or greater antibody suppression.

The results of testing the compounds of this invention for their ability to reduce antibody production are summarized in Table I. Azathioprine (IMURAN), which is used for clinical immunosuppression, has an MED of 100 mg./kg.×9 by this test.

TABLE I

Oral immunosuppressive Activity of 7H—Benzimidazo[2,1-a]benz[de]-isoquinoline-7-ones of Formula II
(Pooled Serum Assay Procedure)

| Compound of Formula II ($R_1$ Substituent) | MED mg./kg. × 9 P.O. |
|---|---|
| 10-trifluoromethyl | 25.0 |
| 11-trifluoromethyl | 0.2 |
| 10-chloro | 3.1 |
| 11-chloro | 0.4 |
| 10-bromo | 12.5 |
| 11-bromo | 1.6 |
| 11-fluoro | 12.5 |
| 10-trifluoromethyl(methyl p-toluenesulfonate salt) | 100 |
| 11-trifluoromethyl(methyl p-toluenesulfonate salt) | 1.6 |
| 10-chloro(methyl p-toluenesulfonate salt) | >100 |
| 11-chloro(methyl p-toluenesulfonate salt) | 100 |
| 11-trifluoromethyl(p-toluenesulfonate salt) | 3.1 |
| 11-chloro(p-toluenesulfonate salt) | 6.25 |

EXAMPLES 20-23

Individual Serum Assay Procedure

In these tests, the procedure described above in Examples 7-19 was modified by the use of 10-mouse groups, rather than 5-mouse groups. The mice were bled as before, but the sera were titered individually rather than as a pool. Mean hemagglutinin values ($log_2$)±S.E. were calculated for each 10-mouse group and p values (by Student's t Test), in comparison with the control group, were determined. The lowest drug dose significantly ($p<0.05$) lowering antibody titer defined the endpoint. The drugs were administered orally in ten daily doses, commencing three days prior to red blood cell injection. Drugs were suspended in a vehicle composed of saline containing 0.125 percent methylcellulose and 0.2 percent nonionic emulsifying agent. Antibody (hemagglutinin) determinations were made seven days following a red blood cell injection. Typical results obtained in the individual serum assay test with representative compounds of the invention are summarized in Table II. Azathioprine has an endpoint dose of 100 mg./kg.×10 P.O. in this assay system.

TABLE II

Oral immunosuppressive Activity of Compounds
(Individual Serum Assay Procedure)

| Compound of Formula II ($R_1$ substituent) | Endpoint Dose ($p<0.05$) in mg./kg. × 10 P.O. |
|---|---|
| 11-trifluoromethyl | 0.4 |
| 11-chloro | 0.2 |
| 11-trifluoromethyl(methyl p-toluene sulfonate salt) | 12.5 |
| 11-bromo | 12.5 |

EXAMPLES 24-28

Graft-Versus-Host (GVH) Reaction

In this test, parental (C57BL) mouse spleen cells are injected into mice of an $F_1$ hybrid strain (C57BL×C3H). The recipient mice do not reject the injected spleen cells, since the hybrid recognizes C57BL-related antigens from its homozygous parent as "self." The injected cells, however, mount a reaction to the recipient's tissue due to the foreign C3H-derived antigens. As a consequence, the recipient's spleen becomes enlarged. Immunosuppression prevents or reduces this enlargement. Thus, spleen weights provide a measure of the GVH reaction and its reduction under immunosuppression.

A modification of Simonsen's original procedure (Ann. N.Y. Acad. Sci., 73, 834 (1958) was employed. Large crops of spleen cells were obtained, without the generally employed manual teasing of spleens, by using Waring blendors with the cutting blades reversed. Two six-second blending periods buffeted the spleens (batches of 25 C57BL spleens in 25-ml. saline) sufficiently to free the cells from the connective tissue. The latter was removed by filtration through several thicknesses of cheesecloth. Cell suspensions prepared in this fashion were standardized, by means of Levy-Hausser chamber counts, to contain $6 \times 10^8$ nucleated cells per ml. Groups of ten 16-18 gram C57BL×C3H mice were injected intraperitoneally with 1 ml. of the donor cell suspension. The compounds were administered either orally (P.O.) or subcutaneously (S.C.) in a vehicle composed of saline containing 0.125% methylcellulose and 0.2% emulphor, commencing 3 days prior to cell injection and continuing daily for 13 days. Control animals received only cells and vehicle. The spleens were removed and weighed 10 days following cell injection, and the mg. spleen/gram body weight was calculated.

The compounds were administered at several dose levels and the mean spleen/body weight ratio at each dose level was compared to the control group which received only the vehicle. The p values (by Student's two-tail t Test) were determined as compared to the control group. The lowest drug dose significantly ($p<0.05$) lowering the spleen/body weight ratio defined the endpoint. The results obtained in the graft-versus-host reaction with the compounds of this invention and standard compounds are summarized in Table III.

TABLE III

Effect of Compounds on GVH Reaction

| Compound of Formula II ($R_1$ substituent) | Route | Endpoint Dose ($p<0.05$) in mg./kg. × 13 |
|---|---|---|
| 11-trifluoromethyl | P.O. | 12.5 |
|  | S.C. | <0.1 |
| 10-trifluoromethyl | P.O. | <25.0 |
| 11-chloro | P.O. | 12.5 |
| 11-bromo | P.O. | <25.0 |
| 11-trifluoromethyl (methyl p-toluenesulfonate salt) | P.O. | 12.5 |
| Standard Compounds |  |  |
| Azathioprine | P.O. | 12.5 |
| Cyclophosphamide | P.O. | 12.5 |
| Cortisone | P.O. | 3.1 |
| Methotrexate | P.O. | 0.2 |

EXAMPLE 29

Adjuvant-induced Arthritis Test in Rats

11-Trifluoromethyl-7H-benzimidazo[2,1-a]benz[de]isoquinoline-7-one was tested for its ability to alter hind paw swelling and bone damage resulting from adjuvant-induced edema in rats. In order to quantitate the inhibition of hind paw swelling resulting from adjuvant-induced arthritis, two phases of inflammation have been defined: (1) the primary and secondary *injected* hind paw, and (2) the secondary *uninjected* hind paw, which generally begins developing about eleven days from the induction of inflammation in the injected paw. Reduction of the latter type of inflammation is an indication of immunosuppressive activity. Cf. Chang, *Arth. Rheum.*, 20, 1135–1141 (1977). Fenoprofen (40 mg./kg.) was included as a standard anti-inflammatory compound for comparative evaluation (Nickander et. al., *Fed Proc. Annual FASEB Mtgs.*, April, 1971, ABS No. 205).

Adjuvant arthritis was induced in male Lewis-Wistar rats (200–210 grams) by a single subplantar injection into the right hind paw of 0.1 ml. of a 0.5% suspension of heat-killed, lyophilized *Mycobacterium tuberculosis* (Calbiochem-Perrigen-C) in mineral oil (a modification of a method reported by Winter et al., *Arth. Rheum.*, 9, 394–397 (1966)). One group of 10 rats ("TB control") received only this treatment. Another group of 5 rats received no treatment (normal control). Each compound to be tested was suspended in carboxymethylcellulose (1%) and administered by gavage to rats (groups of 5 each) in daily oral doses 100 mg./kg. (Test 1) and 50 mg./kg. (Test 2), beginning on day one and continuing through the 23rd day after the adjuvant injection (24 doses). Paw volumes were measured by mercury displacement using a Statham pressure transducer and digital voltmeter. Volumes of both the injected and the uninjected hind paws were measured on days 11, 14, 16, 18, 21, 23, and 25. X-ray photos were taken on day 25, after the animals were sacrificed. The paw volume measurements on the uninjected paw beginning with day 11 through day 25 were computer plotted for the TB controls, the normal controls, and the drug-treated animals, and the areas under the curves [(TB controls minus normal controls) and (treated animals minus normal controls)] were determined. The results are summarized in Table IV.

TABLE IV

Inhibition of Uninjected Paw Volume Inflammation Days 11 through 25

| | Dose Mg./kg. P.O. × 24 | % Inhibition* |
|---|---|---|
| Test 1 | | |
| Fenoprofen | 40 | 44.0% |
| 11-Trifluoromethyl-7H-benzimidazo[2,1-a]benz[de]isoquinoline-7-one | 100 | 85.8% |
| Test 2 | | |
| Fenoprofen | 40 | 60.7% |
| 11-Trifluoromethyl-7H-benzimidazo[2,1-a]benz[de]isoquinoline-7-one | 50 | 55.9% |

*% inhibition is the difference of the areas under the curves (AUC) of the mean uninjected paw volumes plotted for days 11, 14, 16, 18, 21, 23, and 25 according to the following formula:

$$\% \text{ Inhibition} = \left[1 - \frac{\text{(Drug treated AUC)} - \text{(normal control AUC)}}{\text{(TB control AUC)} - \text{(normal control AUC)}}\right] \times 100$$

Gross observation of X-ray photos taken of uninjected paws showed a 94% (Test 1) and 88% (Test 2) inhibition of bone damage in the treated animals as compared to the TB control group. A substantial inhibition of bone damage (68% in Test 1, 66% in Test 2) was also seen in a comparison of the injected paws.

We claim:

1. A method for preparing 10- or 11-trifluoromethyl-7H-benzimidazo[2,1-a]benz[de]isoquinoline-7-one which comprises:
   (Step A) treating naphthalimide with a 4- or 5-trifluoromethyl-substituted o-nitrohalobenzene in an inert solvent at about 50°–200° C. in the presence of an alkali metal carbonate or hydroxide to form the intermediate N-substituted naphthalimide and
   (Step B) reducing the intermediate N-substituted naphthalimide and heating in an inert solvent at about 50°–180° C.

2. A method as described in claim 1 wherein a catalytic amount of an alkali metal halide is included in Step A.

3. A method as in claim 1 or 2 wherein the trifluoromethyl-substituted o-nitrohalobenzene is 4-chloro-3-nitrobenzotrifluoride.

4. A method as in claim 1 or 2 wherein the reduction in step B is accomplished through catalytic hydrogenation.

* * * * *